US011806580B1

(12) United States Patent
Nolan

(10) Patent No.: US 11,806,580 B1
(45) Date of Patent: Nov. 7, 2023

(54) EXERCISE TRAINING SYSTEM AND METHOD OF USE

(71) Applicant: Nicole Nolan, Houston, TX (US)

(72) Inventor: Nicole Nolan, Houston, TX (US)

( * ) Notice: Subject to any disclaimer, the term of this patent is extended or adjusted under 35 U.S.C. 154(b) by 0 days.

(21) Appl. No.: 17/034,947

(22) Filed: Sep. 28, 2020

Related U.S. Application Data

(63) Continuation-in-part of application No. 16/382,831, filed on Apr. 12, 2019, now abandoned.

(51) Int. Cl.
*A63B 24/00* (2006.01)
*G16H 20/30* (2018.01)
*A63B 71/06* (2006.01)

(52) U.S. Cl.
CPC ......... *A63B 24/0075* (2013.01); *G16H 20/30* (2018.01); *A63B 71/0622* (2013.01); *A63B 2024/0081* (2013.01)

(58) Field of Classification Search
CPC ........ A63B 71/0622; A63B 2024/0081; A63B 2024/009–0096; A63B 24/0075–0087; A63B 2225/10–105
See application file for complete search history.

(56) References Cited

U.S. PATENT DOCUMENTS

| | | | | |
|---|---|---|---|---|
| 7,465,257 B1* | 12/2008 | Morgan, Jr. | ............ | A63F 13/33 434/257 |
| 8,105,207 B1* | 1/2012 | Lannon | ............ | A63B 23/03566 482/901 |
| 2003/0032524 A1* | 2/2003 | Lamar | ................ | A63B 21/4029 482/8 |
| 2005/0209050 A1* | 9/2005 | Bartels | ............... | A63B 71/0622 482/8 |
| 2008/0051256 A1* | 2/2008 | Ashby | ................ | A63B 71/0622 482/1 |
| 2008/0242509 A1* | 10/2008 | Menektchiev | ..... | A63B 21/0628 482/99 |
| 2009/0048070 A1* | 2/2009 | Vincent | ................... | G06F 1/163 482/8 |
| 2011/0172060 A1* | 7/2011 | Morales | ............. | A63B 69/0053 482/8 |
| 2012/0108394 A1* | 5/2012 | Jones | ................... | A63B 69/305 482/84 |
| 2012/0277891 A1* | 11/2012 | Aragones | ............. | G09B 19/003 700/91 |
| 2014/0194250 A1* | 7/2014 | Reich | ................. | A63B 24/0084 482/5 |
| 2014/0363800 A1* | 12/2014 | Harris | ................ | G09B 19/0038 434/247 |
| 2015/0133748 A1* | 5/2015 | Edmonds | ............. | A61B 5/0022 600/595 |
| 2016/0129328 A1* | 5/2016 | Findlay | .................. | G09B 19/22 473/422 |
| 2017/0007885 A1* | 1/2017 | Kerwin | ............. | G09B 19/0038 |
| 2017/0165525 A1* | 6/2017 | Tellez | ............... | A63B 71/0622 |
| 2017/0197106 A1* | 7/2017 | Dalebout | ............. | A63B 21/005 |
| 2018/0064992 A1* | 3/2018 | Rothman | ............... | H04N 7/188 |
| 2020/0353312 A1* | 11/2020 | Smith | ............. | A63B 21/00069 |

* cited by examiner

*Primary Examiner* — Nyca T Nguyen
(74) *Attorney, Agent, or Firm* — Avek IP, LLC

(57) ABSTRACT

An exercise system includes a location housing stations; displays, each associated with one of the stations; a platform in communication with the displays, the platform to implement a video through the display; the video is associated with an exercise training; and each display associated with the stations provides a different video for the designated station.

4 Claims, 6 Drawing Sheets

EXERCISE TRAINING SYSTEM AND METHOD OF USE

BACKGROUND

1. Field of the Invention

The present invention relates generally to exercise systems, and more specifically, to an exercise system that allows for split goals and multiple options for users working out in the same class or environment.

2. Description of Related Art

Exercise systems are well known in the art. Common practices include taking classes or following a guided video to partake in an exercise activity. These conventional systems do not always take into account the various needs, goals, and levels of the individuals. For example, a first user may desire to lose weight, while another user desires to gain strength. Both of these goals cannot always be accomplished by the same exercise system at the same time. Similarly, users may have different training backgrounds, and therefore need modified techniques.

It is an object of the present invention to provide an exercise system that allows for split goals. In other words, users with different goals can partake in the same class or workout in the same environment, while being provided with exercise routines that are suitable for their indicated goals.

DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

Figure 1:
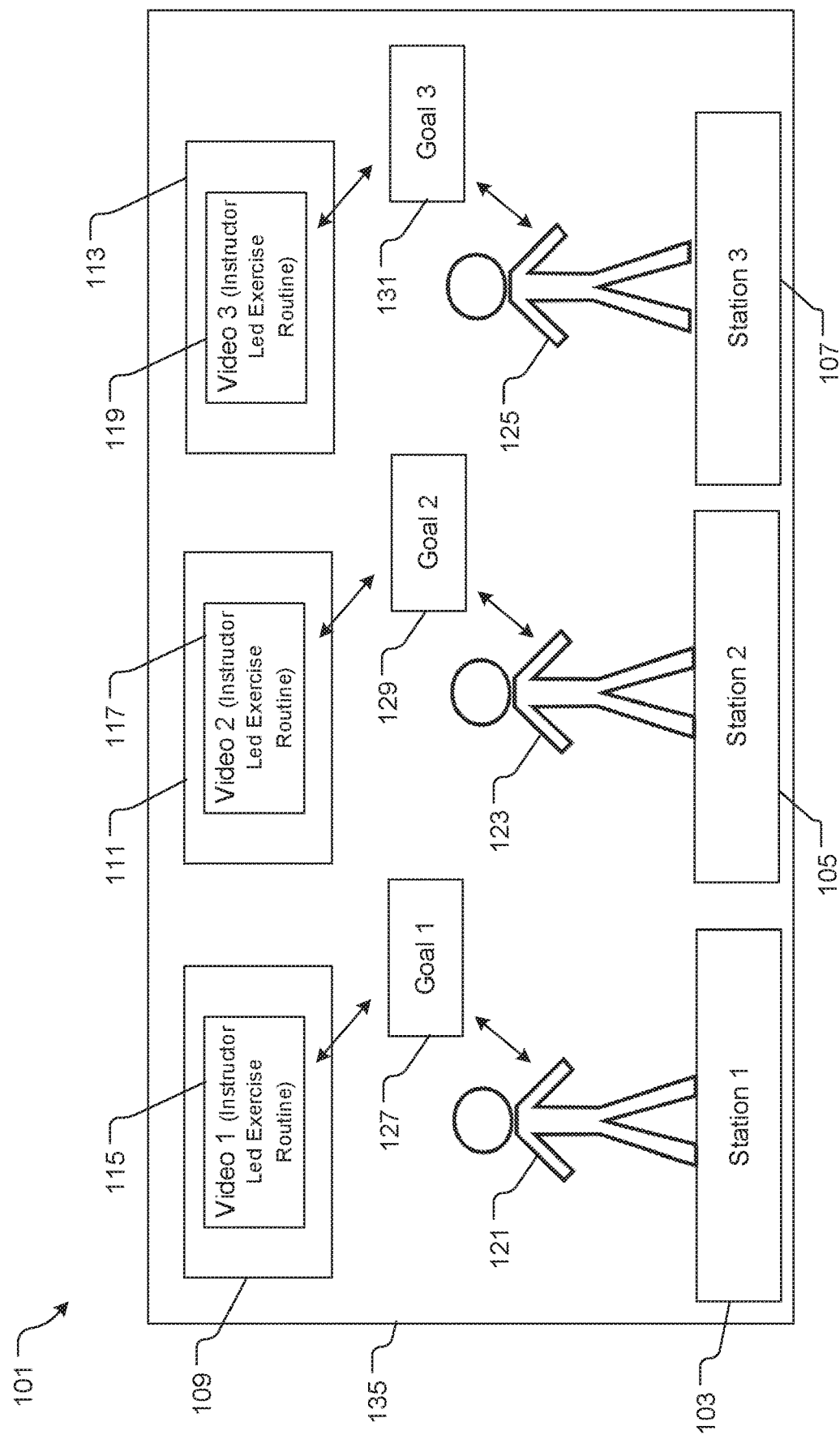
FIG. 1 is a schematic of an exercise system in accordance with a preferred embodiment of the present application.

While the system and method of use of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the present application as defined by the appended claims.

DETAILED DESCRIPTION OF THE PREFERRED EMBODIMENT

Illustrative embodiments of the system and method of use of the present application are provided below. It will of course be appreciated that in the development of any actual embodiment, numerous implementation-specific decisions will be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The system and method of use in accordance with the present application overcomes one or more of the above-discussed problems commonly associated with conventional exercise systems. Specifically, the present invention allows for two or more individuals to workout in the same group, but be provided with instructions that are suitable to their own specified goals or needs. These and other unique features of the system and method of use are discussed below and illustrated in the accompanying drawings.

The system and method of use will be understood, both as to its structure and operation, from the accompanying drawings, taken in conjunction with the accompanying description. Several embodiments of the system are presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless described otherwise.

The preferred embodiment herein described is not intended to be exhaustive or to limit the invention to the precise form disclosed. It is chosen and described to explain the principles of the invention and its application and practical use to enable others skilled in the art to follow its teachings.

Referring now to the drawings wherein like reference characters identify corresponding or similar elements throughout the several views, FIG. 1 depicts a schematic of an exercise system 101 in accordance with a preferred embodiment of the present application. It will be appreciated that system 101 overcomes one or more of the above-listed problems commonly associated with conventional exercise systems.

In the contemplated embodiment, system 101 includes a plurality of stations 103, 105, 107, each having an overhead visual display 109, 111, 113. Each overhead visual display is configured to provide a video 115, 117, 119. In the preferred embodiment, the videos are instructor led exercise routines. Each user 121, 123, 125 of the plurality of stations can provide a goal and/or option 127, 129, 131 for their exercise routine. The system is configured to correlate the goal or needed option of each user with the associated video, thereby providing for a personalized workout that is still in a group setting, but that is configured to help the user meet their individual goals.

As an example, user 121 may have the goal of losing weight. Indication of such a goal will direct the video 115 to provide the user with a lot of cardio and repetition with a lower weight amount. User 123 may have the goal of gaining strength, and as such, video 117 will provide the user with fewer repetitions, but with a larger weight. The system still allows for user 121 and user 123 to be part of the same exercise experience 135, such as a class.

It should be appreciated that one of the unique features believed characteristic of the present application is the use of stations with overhead visuals to provide users with videos that are suitable to their goals or needs, such as different training levels.

Figure 2:
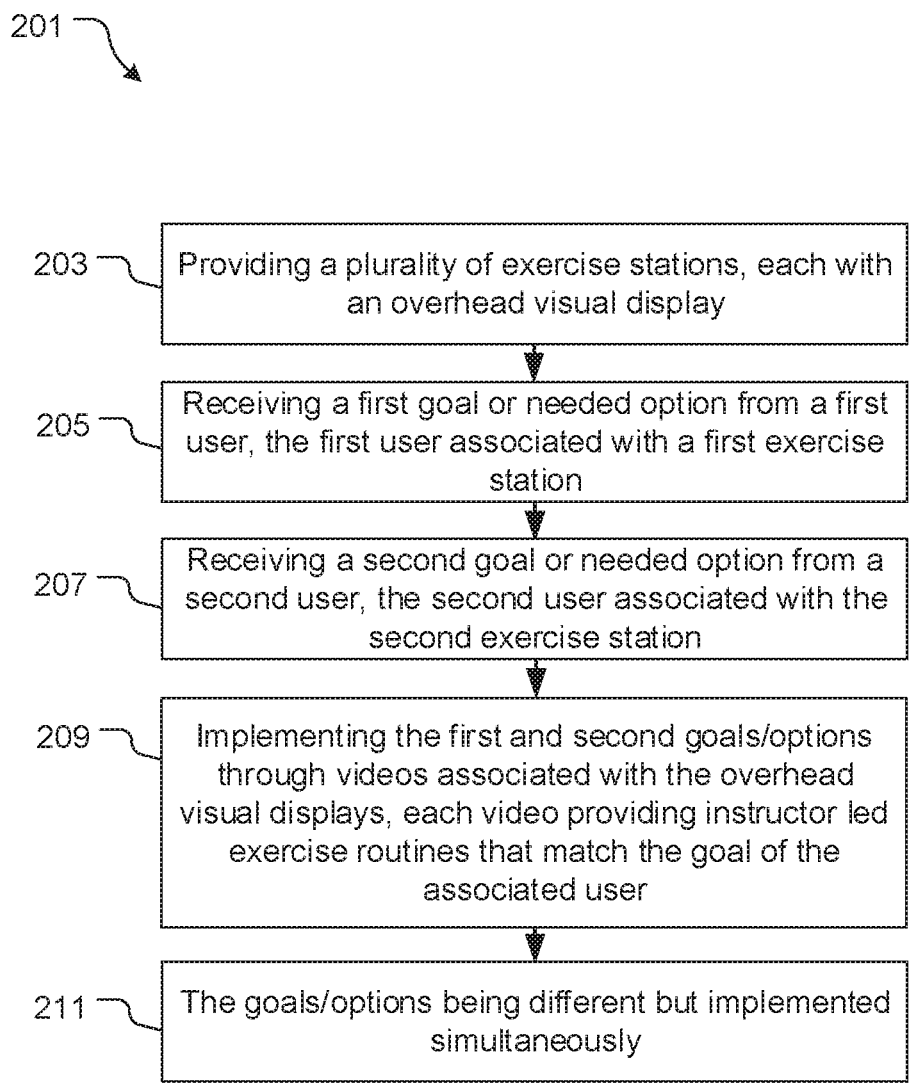
FIG. 2 is a flowchart of a method of use of the system of FIG. 1.

In FIG. 2, a flowchart 201 depicts a method of use of system 101. During use, a plurality of stations are created, wherein each station has an overhead display configured to play a video, as shown with box 203. A first user will provide a first goal or will require a first option, and a second user will provide a second goal or will require a second option (it should be appreciated that the system is suitable for a plurality of users), as shown with boxes 205, 207. The first display will play a video suitable for the first goal/option, while the second display plays a video suitable for the second goal/option, as shown with boxes 209. The goals/options can be different or the same, but the videos are suitable for the goal of the associated user, as shown with box 211.

Figure 3:
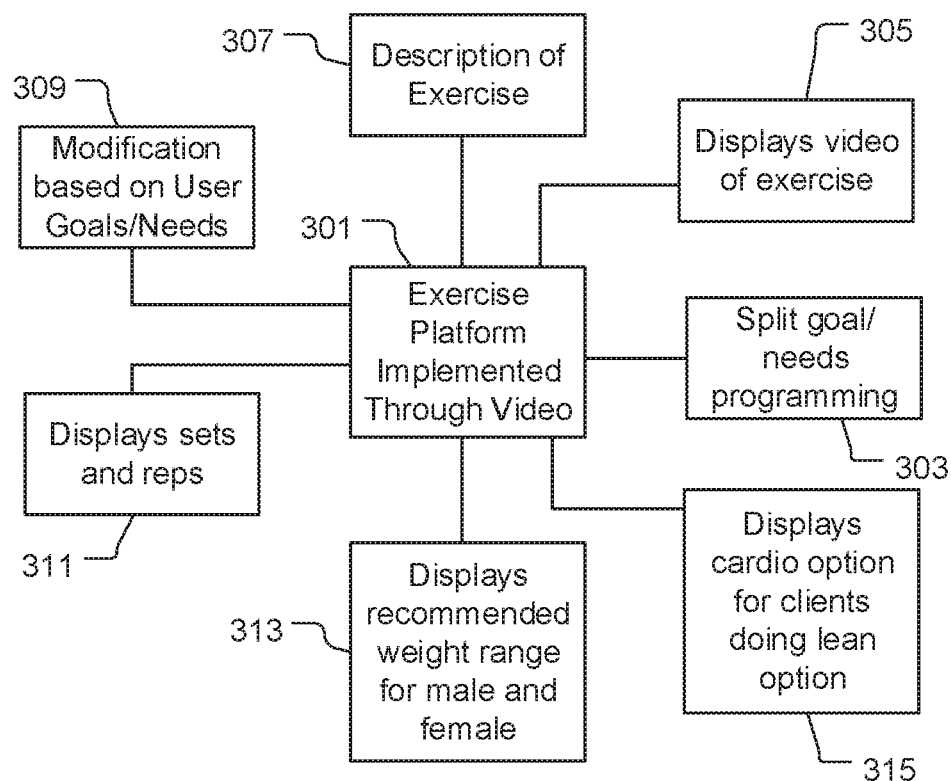
FIG. 3 is a simplified schematic of the features of an exercise platform that works with the video systems of FIG. 1 to provide split goals/options.

In FIG. 3, a simplified schematic depicts the features of a platform 301 that works with the system of FIG. 1, to implement split goal/needs exercise programs 303 through the displays and videos 305 of the present invention. The platform includes the following features, a description of exercises 307, modification of the exercises per the user desired goals/needs 309, a display of reps and sets 311, a display of recommended weight range for male and female 313, and a display of cardio options for users doing the lean option 315.

Figure 4:
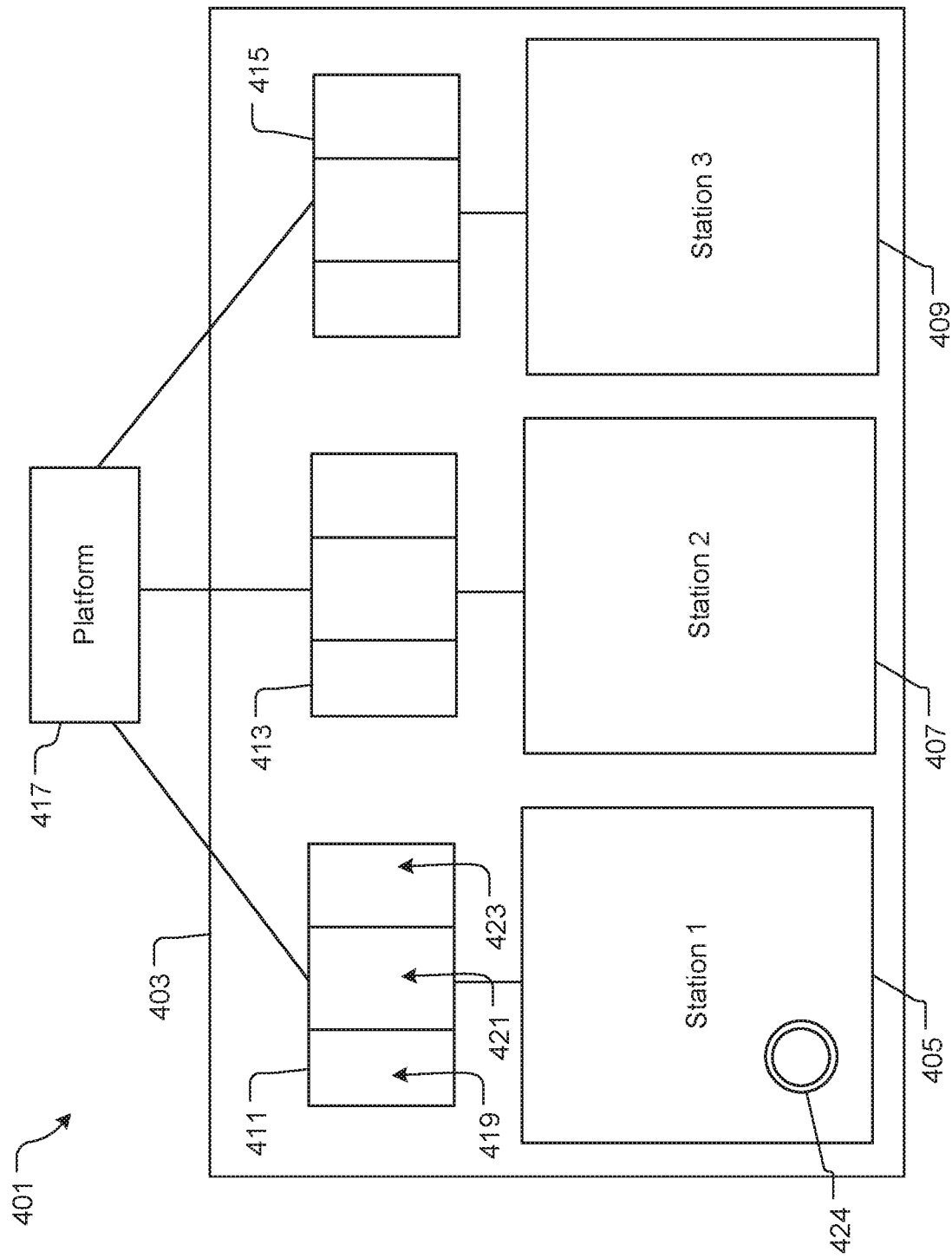
FIG. 4 is a schematic of an alternative embodiment of an exercise system in accordance with the present application.

In FIG. 4, a schematic depicts an alternative embodiment of an exercised training system 401 in accordance with the present application. System 401 is similar in form and function to system 201. System 401 includes a location 403, such as a building which may be a gym, the location 403 housing a plurality of stations 405, 407, 409. In this embodiment, each station is adapted for multiple users, for example, one station may be a weight lifting station, while another station may be a cardio station.

Each station includes a display 411, 413, 415 connected to a platform 417, wherein the platform 417 provides for one or more options 419, 421, 423 to be implemented through the display, the one or more options being videos as previously discussed and explained. The options can provide for various fitness levels, various fitness goals, or various adaptations for an exercise. For example, at a first station 405, which may be a weight lifting station, the display 411, may include a beginner option 413, an intermediate option 415, and an advanced option 417. This allows for multiple users to engage in a training activity together, thereby providing benefits of a group setting, while receiving more customized direction.

In some embodiments, the options 419, 421, 423 may be color coded for ease of use. For example, a new member may focus on a green level, which would be an easy variation, whereas a blue level may be for the more experienced user. In some embodiments, one or more wristbands 424 may also be used, wherein the wristband correlates to one of the options. Again, for example, a green wristband will correlate to a green option, which may be for the beginner user.

It should be appreciated that the platform 417 provides for control of the stations, such as making changes or modifications as necessary.

Figure 5:
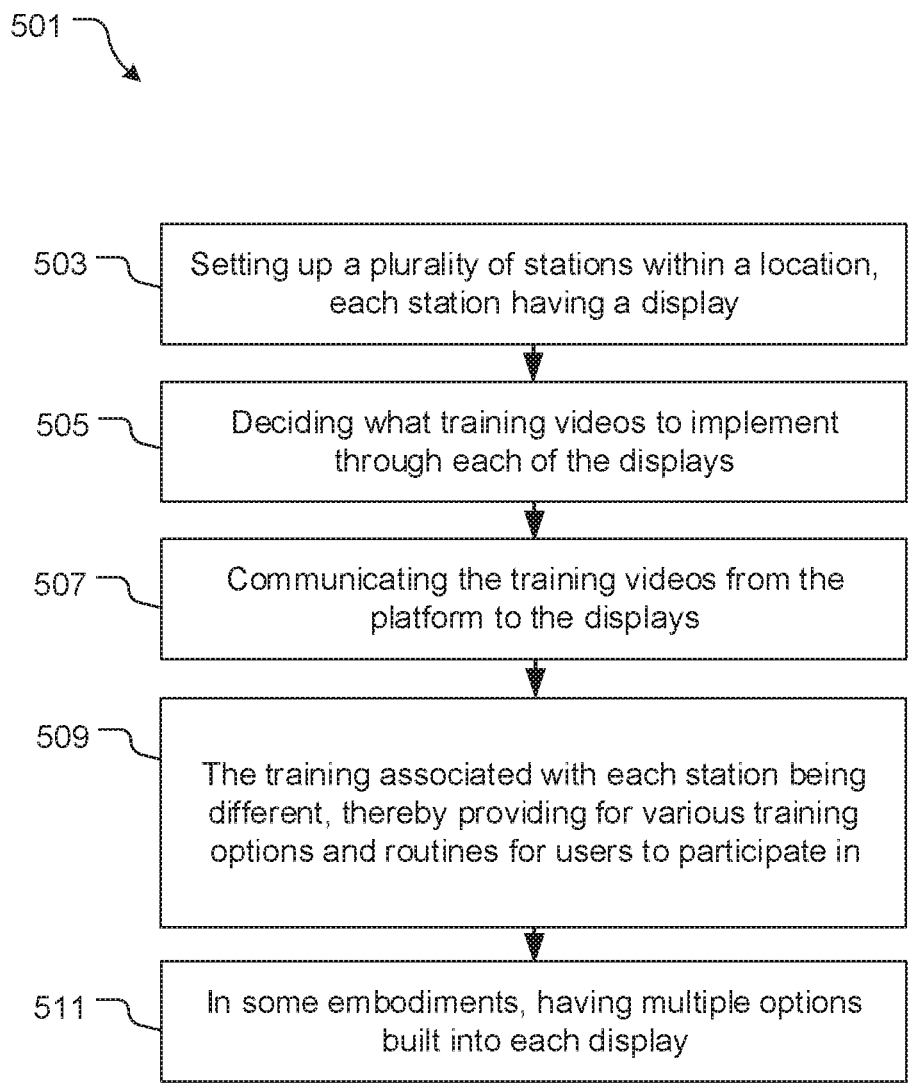
FIG. 5 is a flowchart of the method of use associated with the system of FIG. 4.

In FIG. 5, a flowchart 501 depicts the method associated with system 401. First, the plurality of stations are set up, such as by creating designated areas within a gym, each station having a display, as shown with box 503. A user, such as a gym owner or trainer, will decide on what training videos to implement through each display for each station, as shown with box 505. The training videos are communicated from the platform to the plurality of displays, wherein each display has a different video, as shown with boxes 507, 509. In some embodiments, each display has a plurality of options, such as having a beginner, intermediate, or advanced option, as shown with box 511.

Figure 6:
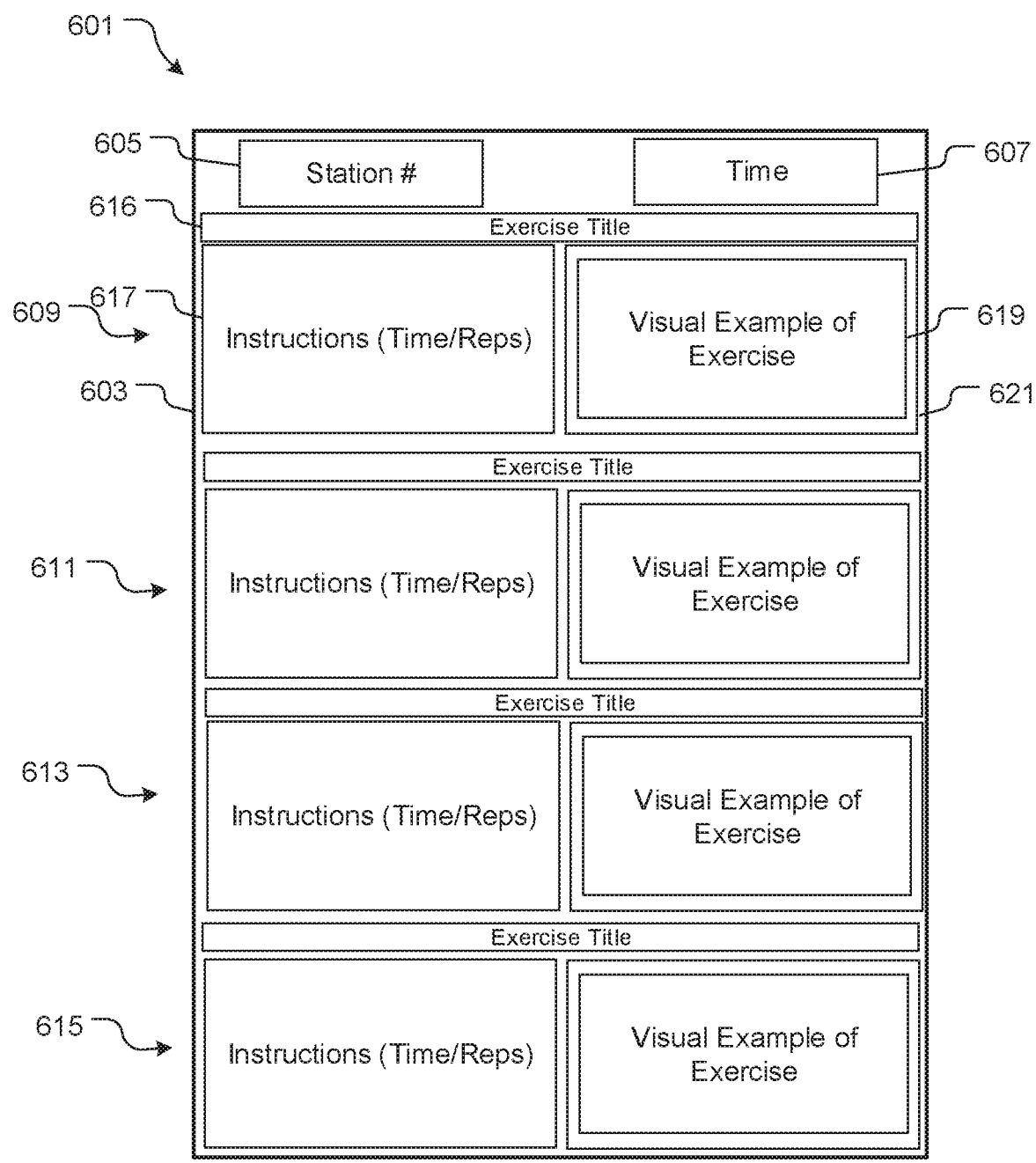
FIG. 6 is a diagram of an exemplary embodiment of a visual display in accordance with the system of FIG. 4.

In FIG. 6, a front view depicts an exemplary embodiment of a display 601 for use with the system of the present invention. As shown, display 601 includes a display screen 603, the display screen being a computerized screen, TV screen, or the like. The display screen 603 having a plurality of information to provide for multiple exercises, multiple levels of exercises, or the like. As shown, the screen 603 can include a station number 605 and a time 607 at the top. The display screen 603 then being broken into the plurality of options 609, 611, 613, 615. Each option 609 may include an exercise title 616, instructions 617, such as a number of reps, or a time interval, or other instructions, and a visual example of the exercise 619. In some embodiments, as discussed, a colored indicator 621 can be provided, the colored indicator telling a user quickly and easily which option is best for them. For example, a green indicator can indicate a beginner option, a yellow indicator can indicate an intermediate option, and a red indicator can indicate an advanced option.

The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments, but are amenable to various changes and modifications without departing from the spirit thereof.

What is claimed is:

1. An exercise system, comprising:
   a location housing a plurality of stations;
   a plurality of displays, each associated with one of the plurality of stations, the plurality of displays are configured to display a video associated with each of the plurality of stations as determined by a goal of a user;
   one or more color-coated options shown through each of the plurality of displays, the one or more color-coated options are related to the goal of the user;
   a color-coated wristband carried by the user, the color-coated wristband is related to the goal of the user; and
   a platform in communication with the plurality of displays, the platform configured to implement a video through the display;
   wherein the video is associated with an exercise training; and
   wherein each display associated with the plurality of stations provides a different video for the designated station.

2. The system of claim 1, wherein the display includes a plurality of options.

3. The system of claim 2, wherein the plurality of options include a beginner option, an intermediate option, and an advanced option; and wherein the color-coated wristbands are related to the plurality of options and are a different color correlating to the beginner option, the intermediate option, and the advanced option.

4. A method of providing exercise training, the method comprising:
- providing the system of claim 3;
- determining a training video to display through each of the plurality of stations, each of the training videos being different;
- communicating the training videos from the platform to the plurality of displays; and
- assigning the training videos to one of a plurality of colors; and
- assigning a goal level to the user, the goal level having a designated color;
- matching the color-coated wristband carried by the user to the designated color; and
- training the user through the training video associated with the designated color.

\* \* \* \* \*

UNITED STATES PATENT AND TRADEMARK OFFICE
CERTIFICATE OF CORRECTION

| | | |
|---|---|---|
| PATENT NO. | : 11,806,580 B1 | |
| APPLICATION NO. | : 17/034947 | |
| DATED | : November 7, 2023 | |
| INVENTOR(S) | : Nicole K. Nolan et al. | |

It is certified that error appears in the above-identified patent and that said Letters Patent is hereby corrected as shown below:

On the Title Page

Item (12) delete "Nolan" and insert -- Nolan et al. --

Item (72) should read:
Nicole K. Nolan of Santa Clarita, CA
Lawrence R. Nolan of Santa Clarita, CA Signed and Sealed this
Third Day of September, 2024

Katherine Kelly Vidal
*Director of the United States Patent and Trademark Office*